United States Patent
Xu

(10) Patent No.: US 8,760,402 B2
(45) Date of Patent: Jun. 24, 2014

(54) MOUSE USED WITH MOUTH

(75) Inventor: Zhen-Wei Xu, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 170 days.

(21) Appl. No.: 13/337,311

(22) Filed: Dec. 27, 2011

(65) Prior Publication Data

US 2013/0076627 A1 Mar. 28, 2013

(30) Foreign Application Priority Data

Sep. 27, 2011 (CN) .......................... 2011 1 0294495

(51) Int. Cl.
*G06F 3/033* (2013.01)
(52) U.S. Cl.
USPC .......................................................... 345/163
(58) Field of Classification Search
USPC .............. 345/156, 157, 159–163; 463/40–60; 341/21–22; 340/4.1; 379/52
See application file for complete search history.

(56) References Cited

U.S. PATENT DOCUMENTS

| 7,091,875 | B2* | 8/2006 | Ondracek | 340/4.11 |
| 7,133,026 | B2* | 11/2006 | Horie et al. | 345/163 |
| 2001/0026266 | A1* | 10/2001 | Schena et al. | 345/163 |
| 2005/0275620 | A1* | 12/2005 | Manal | 345/156 |
| 2007/0085827 | A1* | 4/2007 | Sturtz | 345/157 |
| 2007/0205983 | A1* | 9/2007 | Naimo | 345/160 |
| 2010/0234074 | A1* | 9/2010 | Keski-Jaskari | 455/566 |

* cited by examiner

*Primary Examiner* — Chanh Nguyen
*Assistant Examiner* — Roy Rabindranath
(74) *Attorney, Agent, or Firm* — Novak Druce Connolly Bove + Quigg LLP

(57) ABSTRACT

A mouse includes a main body and a control circuit. A left button, a number of pressure sensors, a right button, and a control button are positioned on the main body. The control circuit includes a control unit, an acceleration sensor, and a wireless transmitter. The left button, the pressure sensors, the right button, the control button, the acceleration sensor, and the wireless transmitter are connected to the control unit. When the mouse is placed in the mouth of a user, the left button, the pressure sensors, and the right button are operated by the tongue of the user. The control button is bitten by the teeth of the user, to turn on the acceleration sensor. The acceleration sensor senses movement of the head of the user, and cooperates with the control unit and the wireless transmitter to control a cursor of a computer to move.

3 Claims, 4 Drawing Sheets

MOUSE USED WITH MOUTH

BACKGROUND

1. Technical Field

The present disclosure relates to mice, and particularly to a mouse used with a mouth.

2. Description of Related Art

A mouse is used to input signals to a computer using manual operations with a hand of a user, which is inconvenient for many people with disabilities.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

The disclosure, including the drawings, is illustrated by way of example and not by way of limitation. References to "an" or "one" embodiment in this disclosure are not necessarily to the same embodiment, and such references mean at least one.

Figure 1:
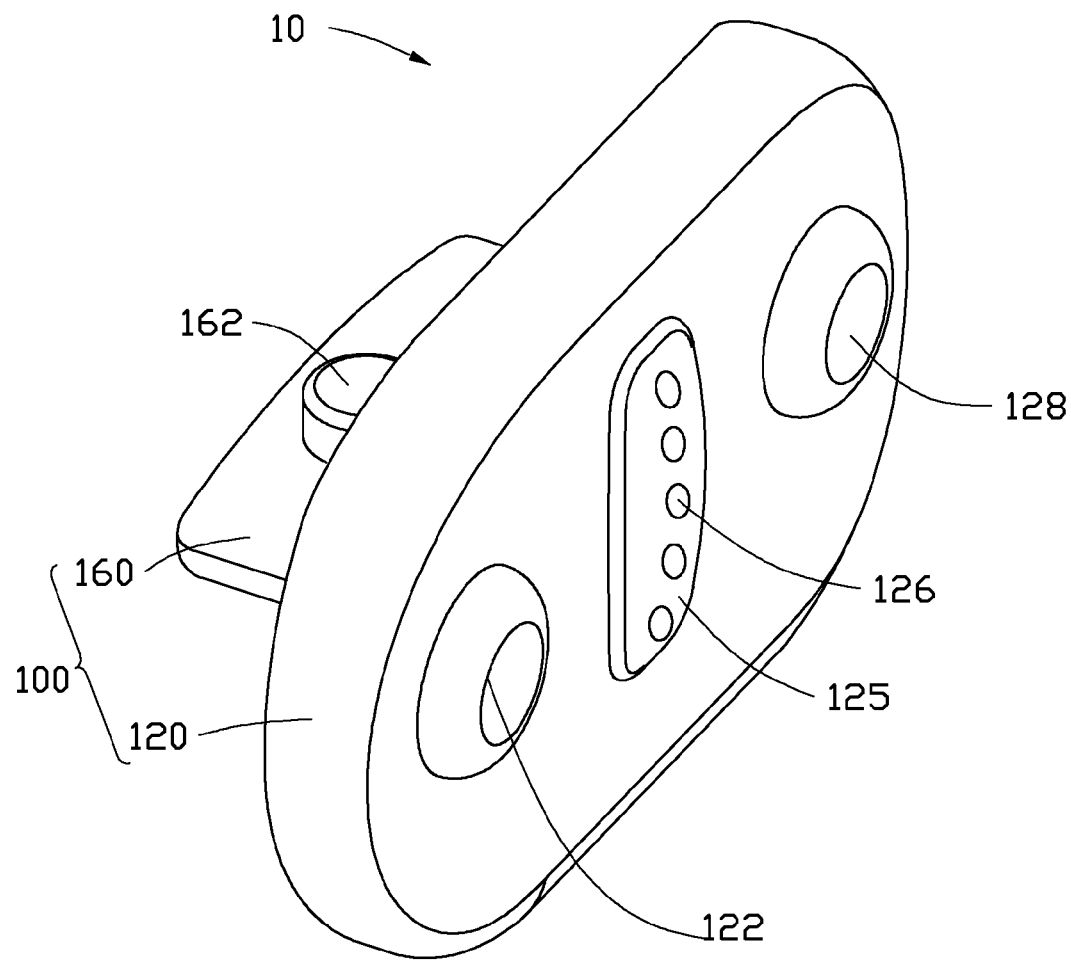
FIG. 1 is an isometric view of a mouse in accordance with an exemplary embodiment of the present disclosure, wherein the mouse includes a control circuit.
Figure 2:
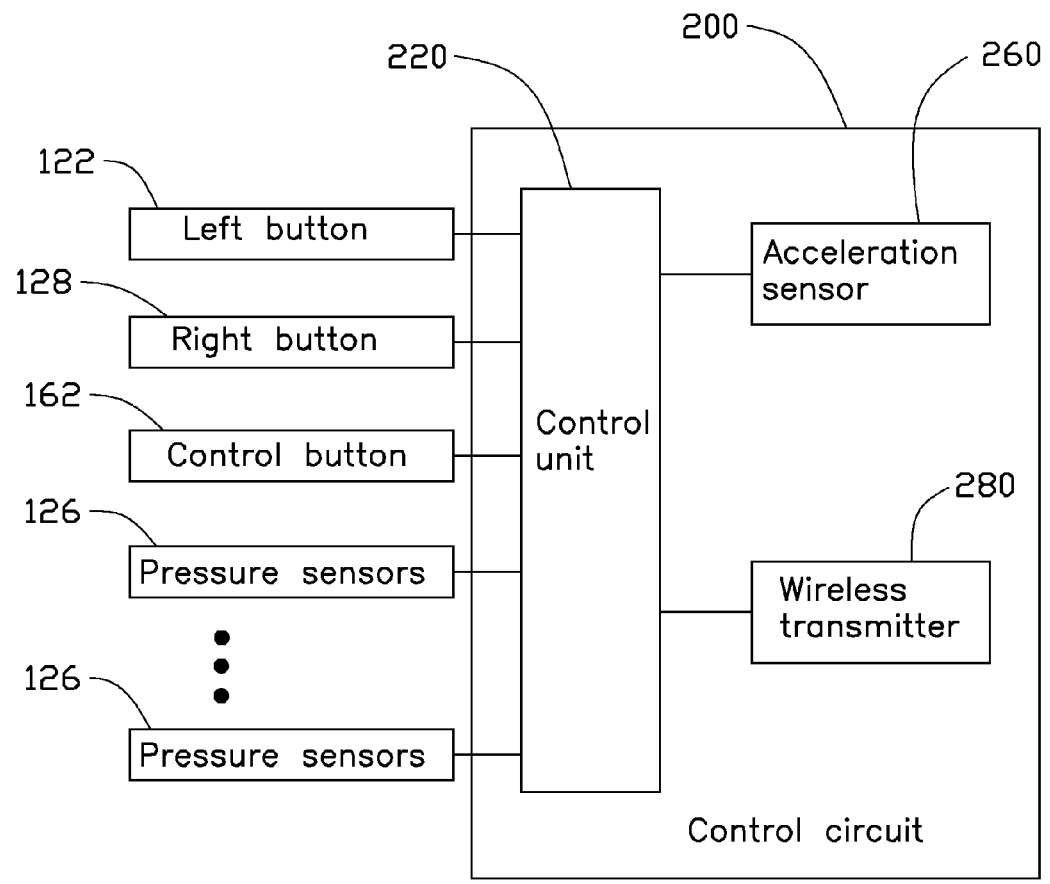
FIG. 2 is a block diagram of the control circuit of FIG. 1.
Figure 3:
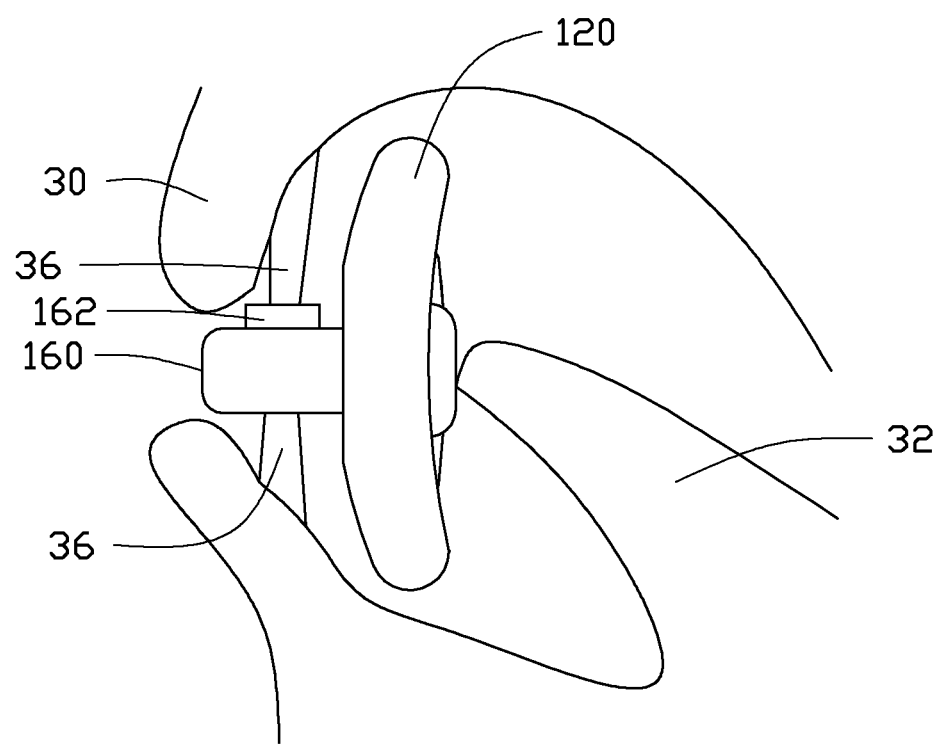
FIG. 3 is a plan view of the mouse of FIG. 1 used in a mouth.
Figure 4:
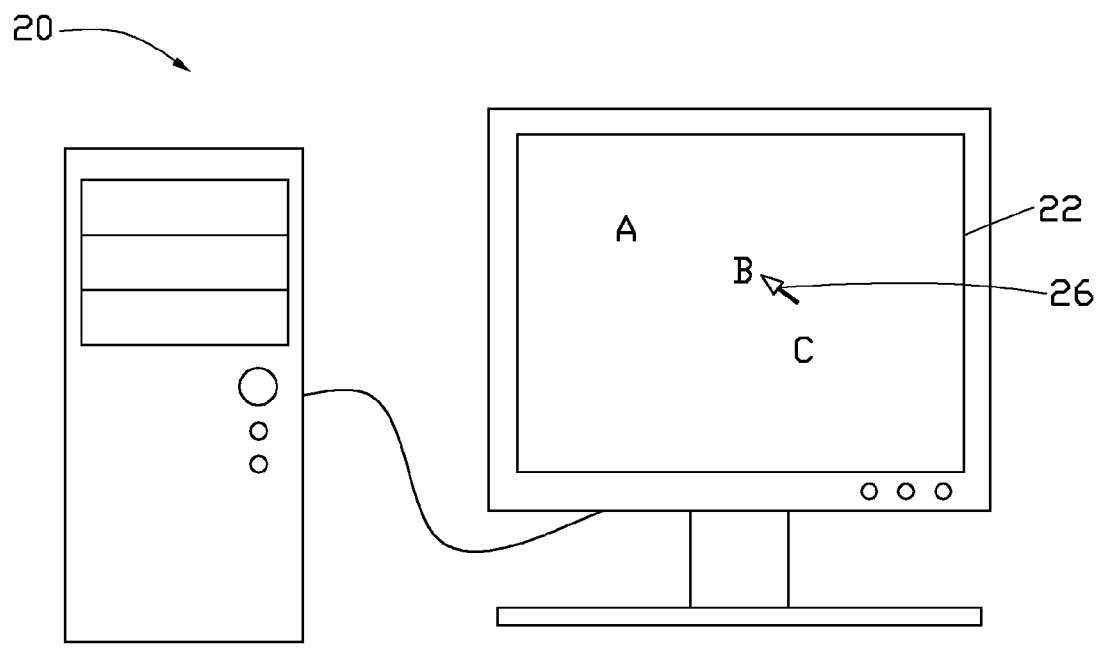
FIG. 4 is an isometric front view of a computer controlled by the mouse of FIG. 1.

FIGS. 1-4, are exemplary embodiments of a mouse 10 including a main body 100 and a control circuit 200 received in the main body 100. The main body 100 is substantially T-shaped, and includes a tongue pressing portion 120 and a bite portion 160 extending perpendicularly from a first side surface of the tongue pressing portion 120. A left button 122, a sliding member 125, and a right button 128 are positioned on a second side surface of the tongue pressing portion 120 opposite to the bite portion 160. A plurality of pressure sensors 126 are positioned on the sliding member 125. A control button 162 is positioned on the top surface of the bite portion 160. The control circuit 200 includes a control unit 220, an acceleration sensor 260, and a wireless transmitter 280. The left button 122, the pressure sensors 126, the right button 128, the control button 162, the acceleration sensor 260, and the wireless transmitter 280 are all connected to the control unit 220. The control unit 220 controls the wireless transmitter 280 to transmit signals to a computer 20 according to signals received from the left button 122, the pressure sensors 126, the right button 128, the control button 162, and the acceleration sensor 260.

In one embodiment, the main body 100 is sealed and made of soft waterproof material. The tongue pressing portion 120 is substantially oval-shaped and arced, and bent toward the bite portion 160 at a certain degree of curvature, to facilitate the mouse 10 being placed in a mouth. The left button 122 and the right button 128 are positioned near two opposite edges of the second side surface of the tongue pressing portion 120; the sliding member 125 is positioned between the left button 122 and the right button 128 on the second side surface. This arrangement of the left and right buttons 122, 128 and the sliding member 125 will facilitate a tongue 32 pressing the left button 122, the sliding member 125, and the right button 128 when the mouse 10 is inserted in the mouth 30 with the second side surface of the tongue pressing portion 120 facing the back of the mouth 30. The control button 162 is positioned on the middle of the top surface of the bite portion 160. This arrangement of the control button 162 will facilitate teeth 36 biting the control button 162 when the mouse 10 is inserted in the mouth 30 with the bite portion 160 between the upper and lower jaws. The control circuit 200 is positioned on a circuit board received in the main body 100. The circuit board includes a battery to supply power for the mouse 10. Five pressure sensors 126 are linearly positioned on the sliding member 125 from top to bottom. In other embodiments, the number of the pressure sensors 126 may be adjusted according to actual need.

In use, the mouse 10 is placed in the mouth 30 of a user. The user can press the left button 122, the sliding member 125, and the right button 128 using the tongue 32. The user can bite the control button 162 using the teeth 36. It may be understood that, if the user do not have teeth, the user can press the control button 162 using his or her lips or gums.

When the tongue 32 slides on the sliding member 125 in a first direction, such as a downward direction, to press the five pressure sensors 126 in turn, the five pressure sensors 126 transmit sensed first pressure signals to the control unit 220 in sequence. After receiving the first pressure signals, the control unit 220 controls the wireless transmitter 280 to transmit a first signal to the computer 20, to control an image, such as a text, a web page, or a picture, displayed on a monitor 22 of the computer 20 to move towards a second direction, such as a downward direction. This is done according to the time sequence of receiving the first pressure signals from the five pressure sensors 126. When the tongue 32 slides on the sliding member 125 in a third direction, such as an upward direction, to press the five pressure sensors 126 in turn, the five pressure sensors 126 transmit sensed second pressure signals to the control unit 220 in sequence. After receiving the second pressure signals, the control unit 220 controls the wireless transmitter 280 to transmit a second signal to the computer, to control an image displayed on the monitor 22 to move towards a fourth direction, such as an upward direction, according to the time sequence of receiving the second pressure signals from the five pressure sensors 126. The above described process is similar to operating a scroll wheel of an existing mouse.

When the control button 162 is bitten using the teeth 36, and the head of the user is moved, the acceleration sensor 260 is turned on to sense the movement of the head of the user, and transmits the sensed movement signal to the control unit 220. After receiving the movement signal, the control unit 220 controls the wireless transmitter 280 to transmit a third signal to the computer 20, to control a cursor 26 displayed on the monitor 22 to move with movement of the head. When the teeth 360 do not bite the control button 162, the acceleration sensor 260 is not turned on, the cursor 26 does not move with movement of the head. Functions achieved by using the tongue 32 to press the left button 122 and the right button 128 is similar to functions achieved by using fingers to click a left button and a right button of an existing mouse. These functions fall within well-known technologies, and are therefore not described here.

As detailed above, the mouse 10 can be placed in the mouth 30 of the user and operated by the tongue 32 and the teeth 36 of the user. Therefore, it is convenient for people with disabilities to use the mouse 10.

Even though numerous characteristics and advantages of the disclosure have been set forth in the foregoing description, together with details of the structure and function of the disclosure, the disclosure is illustrative only, and changes may be made in detail, especially in the matters of shape, size, and arrangement of parts within the principles of the disclosure to the full extent indicated by the broad general meaning of the terms in which the appended claims are expressed.

What is claimed is:

1. A mouse comprising:
    a main body comprising a plurality of pressure sensors and a control button; and
    a control circuit received in the main body, the control circuit comprising a control unit, an acceleration sensor, and a wireless transmitter;
    wherein the pressure sensors, the control button, the acceleration sensor, and the wireless transmitter are connected to the control unit;
    wherein when the mouse is placed in the mouth of a user, the pressure sensors sense pressure of the tongue of the user pressing the pressure sensors, and transmit sensed pressure signals to the control unit, the control unit controls the wireless transmitter to transmit a first signal to a computer according to a time sequence of receiving the pressure signals from the pressure sensors, to control an image displayed on a monitor of the computer to move;
    wherein the control button turns on the acceleration sensor when the teeth of the user bite the control button, the acceleration sensor senses movement of the head of the user, and transmits sensed movement signal to the control unit, the control unit controls the wireless transmitter to transmit a second signal to the computer according to the movement signal received from the acceleration sensor, to control a cursor displayed on the monitor to move with movement of the head; and
    wherein the main body is substantially T-shaped, and comprises a tongue pressing portion and a bite portion extending perpendicularly from a first side surface of the tongue pressing portion, a left button, a sliding member, and a right button are positioned on a second side surface of the tongue pressing portion opposite to the bite portion, the pressure sensors are positioned on the sliding member, the control button is positioned on the top of the bite portion, the left button and the right button function as the left button and right button of an existing mouse, and are operable by the tongue.

2. The mouse of claim 1, wherein the main body is sealed and made of soft waterproof material, and the tongue pressing portion is substantially oval-shaped and arced, and bent toward the bite portion, to facilitate the mouse being placed in the mouth.

3. The mouse of claim 1, wherein the pressure sensors are linearly positioned on the sliding member from top to bottom.

* * * * *